United States Patent [19]

Cork

[11] Patent Number: 4,666,852

[45] Date of Patent: May 19, 1987

[54] PHOTOSYNTHETIC BIOCONVERSION SULFUR REMOVAL

[75] Inventor: Douglas J. Cork, Chicago, Ill.

[73] Assignee: Institute of Gas Technology, Chicago, Ill.

[21] Appl. No.: 401,527

[22] Filed: Jul. 26, 1982

[51] Int. Cl.[4] .................. D06M 16/00; A61L 9/01; C10G 32/00; C02F 3/00

[52] U.S. Cl. ................................................. 435/262

[58] Field of Search ............. 435/140, 166, 167, 253, 435/262, 264, 266, 281, 282, 801, 813; 210/601

[56] References Cited

U.S. PATENT DOCUMENTS

| | | | |
|---|---|---|---|
| 1,701,825 | 2/1929 | Seil | 435/266 |
| 3,020,205 | 2/1962 | Jensen | 435/168 |
| 3,105,014 | 9/1963 | Harrison | 166/246 |
| 4,022,665 | 5/1977 | Ghosh et al. | 435/140 |
| 4,124,501 | 11/1978 | Yen et al. | 210/605 |
| 4,135,976 | 1/1979 | Kitajima | 435/168 |
| 4,200,523 | 4/1980 | Balmat | 210/611 |

OTHER PUBLICATIONS

Cork et al: Chem. Abstr. 90:3024e, (1979), of Metall. Appl. Bact. Leaching Relat. Microbiol. Phenom., 1977, pp. 207–221.

Cork et al: Chem. Abstr. 92:28098m, (1980), of Dev. Ind. Microbiol. 20, 591 (1979).

Cork: Diss. Abstr. 39 B, 4480-B (1979).

Pearson, M. J., "Developments in Claus Catalysts", Hydrocarbon Processing, Feb., 1973, pp. 81–85.

Kirk, A. T. and Othmer, B. A., Encyclopedia of Chemical Technology, vol. 19, John Wiley & Sons, N.Y., 386, 1969.

Atwood, R. G., D. C. Swaim, Jr., and C. M. Yon, "New Integrated UCAP Process Treats Low—$H_2S$ Streams, Trims Emission", Oil and Gas Journal, 77, 1979, pp. 111–114.

Slack, A. W. and G. A. Hollinden, "Sulfur Dioxide Removal from Waste Gases", Noyes Data Corporation, Park Ridge, New Jersey, 1975, p. 165.

Fleming, D. K., "Acid-Gas Removal Systems in Coal Gasification", Symposium on Ammonia from Coal, National Fertilizer Development Center, Tennessee Valley Authority, Muscle Schoals, Ala., 1979.

Ellwood, P., "Metavandates Scrub Manufactured Gas", Chemical Engineering, 71, Jul. 20, 1964, pp. 128–130.

Vasan, Srini, "Holmes-Stretford Process Offers Economic $H_2S$ Removal", The Oil and Gas Journal, 76, Jan. 2, 1978, pp. 78–80.

Cork, D. J., "Bioconversion of Coal Acid Gas to Biomass and Chemicals", Midwest Energy Conference on Liquid Fuels from Coal and Biomass, Midwest Universities Energy Consortium, Ohio State University, Columbus, Ohio, Oct. 5–6, 1981.

Cork, D. J., M. A. Cusanovich, "Sulfate Decomposition: A Microbiological Process", pp. 207–221, Metallurgical Applications of Bacterial Leaching and Related Microbiological Phenomena, L. E. Murr, A. E. Torma, J. E. Bierley, eds., Academic Press, N.Y., 1978.

(List continued on next page.)

Primary Examiner—James Martinell, Ph.D.
Attorney, Agent, or Firm—Thomas W. Speckman

[57] ABSTRACT

This invention relates to a process for sulfur removal from gas streams by contacting an active culture of photosynthetic sulfur bacteria with reductive sulfur compounds and carbon oxides in the gas stream under substantially anaerobic conditions with irradiation by electromagnetic energy and cultivating the bacteria to form elemental sulfur and organic carbon compounds. The process is particularly suited for removal of hydrogen sulfide from acid-gas streams and from natural or raw pipeline gas with greater than 95 percent and usually greater than about 98 percent sulfur removal from gas streams. The process is operable with gas streams of very low hydrogen sulfide content of about 0.1 and less Mole percent and gas streams of high hydrogen sulfide content. The process utilizes Chlorobium bacteria to produce elemental sulfur and organic carbon compounds which may be advantageously utilized to produce hydrocarbon fuels.

15 Claims, 4 Drawing Figures

OTHER PUBLICATIONS

Cork, D. J., M. A. Cusanovich, "Continuous Disposal of Sulfate by a Bacterial Mutualism", pp. 37-48, *Developments in Industrial Microbiology*, Society for Industrial Microbiology, 1979.

Kinetics of Sulfate Conversion to Sulfur by a Bacterial Mutualism: A Hydrometallurgical Application, Cork, D. J., PhD, Dissertation, University of Arizona, Tucson, 1978.

Cork, D. J., "Acid Waste Gas Bioconversion—An Alternative to the Claus Process", paper at 23rd Annual Meeting of Society for Industrial Microbiology, Richmond, Va., Aug. 9-14, 1981, published in Developments in Industrial Microbiology, Society for Industrial Microbiology, 23, 1981, pp. 379-387.

Cork, D. J. and Sauchen, M. A., "Bioprocess for Fossil Fuel Acid Gas Bioconversion—*An Alternative to the Stretford Process*", paper at 4th Symposium on Biotechnology and Energy Production and Conservation, Gatlin, Tennesse, May 11-14, 1982.

PHOTOSYNTHETIC BIOCONVERSION SULFUR REMOVAL

BACKGROUND OF THE INVENTION

1. Field of the Invention

This invention relates to a process for sulfur removal from gas streams which comprise reductive sulfur compounds and carbon oxides by photosynthetic bioconversion forming elemental sulfur and organically fixed carbon compounds. The process provides greater than 90 to 99 percent sulfur removal with simultaneous organic hydrocarbon production by contacting such gas streams with photosynthetic sulfur bacteria under anaerobic conditions with electromagnetic irradiation. The process is particularly well suited for removal of hydrogen sulfide from acid gas containing streams, such as produced in fossil fuel hydrogasification or hydroliquefaction processes or in hydrogen sulfide removal from natural gas.

2. Description of the Prior Art

Many chemical processes, such as fossil fuel conversion processes, produce effluents that contain sulfur compounds, usually predominantly hydrogen sulfide. Natural or synthetic pipeline gases usually contain hydrogen sulfide which must be removed prior to transmission due to its poisonous nature. The hydrogen sulfide must be removed, in the case of fuels, in order to meet sulfur oxide emission requirements when the fuel is burned.

An important process for sulfur recovery has been the Claus process and various modifications thereof as described widely in literature, such as Wall, J. et al, "NG/LNG/SNG Handbook", Hydrocarbon Processing, pgs. 90–102 and 107–116, April, 1973; Dearson, J. J. "Developments in Claus Catalysis", *Hydrocarbon Processing*, pgs. 81–85, February, 1973; Kirk, A. T. and Othmar, B. A. Encyclopedia of Chemical Technology, Vol. 19, John Wiley & Sons, New York, 386, 1969; and Atwood, R. G., D. C. Swaim Jr., and C. M. Yon, "New integrated UCAP Process treats low - H$_2$S streams, trims emission", Oil and Gas Journal, 77, pgs. 111–114, 1979. Claus sulfur removing processes have been able to attain 90 to 95 percent sulfur recovery under ideal operating conditions with 3 and 4 stage units claiming up to 97 percent recovery. To achieve higher degrees of recovery and to meet air pollution standards has required installation of add-on tail-gas treating units. The Claus process has been applied to acid gas streams containing varying amounts of hydrogen sulfide, but is relatively inefficient in its operation at lower concentrations of hydrogen sulfide as evidenced by the requirement of the tail-gas cleaning processes which have been described in Slack, A. W. and G. A. Hollinden, "Sulfur Dioxide Removal from Waste Gases", *Noyes Data Corporation*, Park Ridge, N.J., pg. 165, 1975. The Claus process has been most effective on feed streams containing at least 15 mole percent hydrogen sulfide as more fully reported in Fleming, D.K., "Acid-gas removal systems in coal gasification" *Symposium on Ammonia from Coal*, National Fertilizer Development Center, Tennessee Valley Authority, Muscle Schoals, Alabama, May 8–10, 1979. Another process is the Stretford process developed for the removal of hydrogen sulfide from coal gas and its conversion to sulfur as described in Ellwood, P. "Metavanadates Scrub Manufactured Gas", *Chemical Engineering*, 71, pgs 128–130, July 20, 1964; and Visan, Srini, "Holmes-Stretford Process Offers Economic H$_2$S Removal", *The Oil and Gas Journal*, 76, pgs. 78–80, Jan. 2, 1978. Another process for high removal of hydrogen sulfide from gas streams, particularly those with low initial hydrogen sulfide concentration and/or high carbon dioxide/hydrogen sulfide ratios, is the Takahax sulfur recovery process as described in Wall, J. et al, supra. Another sulfur recovery process for continuous removal of hydrogen sulfide from natural gas or synthesis gas is the Giammarco Vetrocoke process described in Wall, J. et.al, supra. A more complete review of these processed is found in Cork, D. J., "Bioconversion of coal acid gas to biomass and chemicals", *Midwest Energy Conference on Liquid Fuels from Coal and Biomass*, Midwest Universities Energy Consortium, Ohio State University, Columbus, Ohio, October 5–6, 1981.

Removal of undesired sulfur compounds from gas and liquid streams by various microorganisms has been previously recognized. U.S. Pat. No. 1,701,825 teaches oxidation of hydrogen sulfide and its removal by Thiobacillus which oxidizes the hydrogen sulfide to sulfuric acid. The reduction of sulfate to sulfide ions by Desulfovibrio and breaking down of organic carbon containing materials has been suggested in dilute aqueou streams as taught by U.S. Pat. No. 4,200,523; oil retort water as taught by U.S. Pat. No. 4,124,501; waste water and oil formations as taught by U.S. Pat. No. 3,105,014; and sulfur containing ores as taught by U.S. Pat. No. 3,020,205.

Sulfate removal by sulfate reduction using Desulfovibrio biological cultures established mutualistically with either Chromatium or Chlorobium for production of elemental sulfur has been suggested. Lactic acid and raw sewage are taught as being suitable carbon sources for the sulfate reduction and cell growth. In this work a pure biological culture of Desulfovibrio converted Sulfate and lactic acid to hydrogen sulfide and carbon dioxide, respectively. The Chlorobium converted 88 percent of the H$_2$S to elemental sulfur. This and similar work is more fully described in Cork, D. J., M. A. Cusanovich, "Sulfate Decomposition: A Microbiological Process", pgs. 207–221, *Metallurgical Applications of Bacterial Leaching and Related Microbiological Phenomena*, L. E. Murr, A. E. Torma, and J. E. Bierley, eds., Academic Press, Inc., New York, 1978, and Cork, D. J., M. A. Cusanovich, "Continuous Disposal of Sulfate by a Bacterial Mutualism", pgs. 37–48, *Developments in Industrial* Microbiology, Society for Industrial Microbiology, 1979. Under static batch conditions Chlorobium have been found to metabolize a maximum of about 4 to about 8 milli-Moles hydrogen sulfide per gram bacteria in as long as a two week period. Kinetics of Sulfate Conversion to Sulfur by a Bacterial Mutualism: A Hydrometallurgical Process, Cork, D. J., PhD Dissertation, University of Arizona, Tucson, 1978.

It has not, however, been previously recognized that the Chlorobium microorganisms can advantageously live in a hydrogen sulfide-carbon dixide gas continuously purged environment such as derived from an acid-gas effluent stream, nor has it been recognized that in a hydrogen sulfide-carbon dioxide gas environment there can be very rapid growth of Chlorobium with high rate simultaneous production of elemental sulfur and organic fixed carbon compounds from gas streams comprising about 0.1 mole percent to as high as about 40 to 65 mole percent hydrogen sulfide and in the presence of large excesses of C0$_2$ to produce in excess of 95 percent hydrogen sulfide removal, and usually in excess of 99 percent removal. In accordance with the present invention more than about 45 milli-Mole $H_2S$ and up to the range of 80 milli-Moles $H_2S$ are metabolized per gram of photosynthetic sulfur bacteria in relatively short detention times.

Various aspects of the Cork process using Chlorobium microorganisms for removal of hydrogen sulfide from fossil fuel acid gas has been described in Cork, D. J., "Acid Waste Gas Bioconversion—An Alternative to the Claus Process", paper at 23rd Annual meeting of Society for Industrial Microbiology, Richmond, Va., Aug. 9-14, 1981 and published in Developments in Industrial Microbiology, Society for Industrial Microbiology, 23, pgs. 379-387, 1981; Cork, D. J., "Bioconversion of Coal Acid Gas to Biomass and Chemicals" paper at Midwest Energy Conference on Liquid Fuels from Coal and Biomass, Midwest Universities Energy Consortium, Columbus, Ohio, Oct. 5-6, 1981; and Cork, D. J. and Sauchen, M. A., "Bioprocess for Fossil Fuel Acid Gas Bioconversion—An Alternative to the Stretford Process" paper at 4th Symposium on Biotechnology and Energy production and Conservation, Gatlinberg, Tenn., May 11-14, 1982.

U.S. Pat. No. 4,135,976 teaches Chlorobium to be suitable to concentrate silver from waste photographic fixing solutions containing silver thiosulfate complex salt by application of the photosynthetic sulfur bacteria under anaerobic conditions with irradiation of light. To attain the growth conditions for the bacteria, municipal sewage or the like must be added to the waste fix solution. The process provides for the recovery of silver together with the purification or decontamination of the photographic processing effluent.

SUMMARY OF THE INVENTION

This invention relates to a process for sulfur removal from gas streams which comprise reductive sulfur compounds and carbon oxides. The streams are contacted with an active culture of photosynthetic sulfur bacteria under substantially anaerobic conditions with irradiation by electromagnetic radiation. The bacteria are cultivated to form elemental sulfur from the reductive sulfur compounds and simultaneously produce fixed organic carbon compounds from the carbon oxides. The process of this invention provides greater than 90 and generally greater than 95 to 98 and up to substantially 100 percent sulfur removal with simultaneous organic production from hydrogen sulfide-carbon dioxide containing streams from a variety of chemical processes, such as acid-gas streams produced in fossil fuel hydrogasification or hydroliquefaction processes and in raw or natural gas production. The process of this invention utilizes bacteria of the Genus Chlorobium to form the elemental sulfur and organic carbon compounds. Although the prior art has taught that $H_2S$ may be suitably generated with $CO_2$ in stoichiometric relation by biological sulfate reduction and utilized by Chlorobium, this is not a necessary feature nor a contemplated source for the process of this invention which prefers large excesses of $CO_2$.

In one embodiment, the process is used in combination with two-phase anaerobic methane digestion to provide easy separation of the elemental sulfur and acetates by acid phase digestion and formation of methane from the acetate radical in the methanogenic phase. In another embodiment, the photosynthetic irradiation is followed by a dark reactor stage for easy separation of the elemental sulfur from the organic carbon compounds.

It is one object of this invention to provide a process for high efficiency removal of reductive sulfur compounds, particularly $H_2S$, from chemical process and effluent streams.

Another object of this invention is to provide a process for greater than 95 and preferably greater than 98 percent sulfur removal from $H_2S$ containing gas streams wherein the $H_2S$ component ranges from about 0.1 to about 65 mole percent.

Yet another object of this invention is to provide a high efficiency $H_2S$ removal process for removal of $H_2S$ from natural or raw pipeline gas containing as high as 50 mole percent $H_2S$.

Still another object of this invention is to provide a high efficiency sulfur removal process which simultaneously utilizes $CO_2$ from acid-gas streams to produce useful organic carbon compounds.

Yet another object of this invention is to provide a high efficiency process for sulfur removal from gas streams using photosynthetic bioconversion achieved by the microorganism of the Genus Chlorobium.

Still another object of this process is to form elemental sulfur and organic carbon compounds from gas streams which comprise reductive sulfur compounds and carbon oxides by reaction in an active culture of Chlorobium with electro-magnetic irradiation in combination with two stage anaerobic methanogenic fermentation to provide easy separation of elemental sulfur from formed organic carbon compounds and production of useful methane containing gas from such organic carbon compounds.

Still another object of this process is to form elemental sulfur and organic carbon compounds from gas streams which comprise reductive sulfur compounds and carbon oxides by reaction with an active culture of Chlorobium with electro-magnetic irradiation in combination with a dark reactor phase forming readily separable elemental sulfur and acetic acid.

BRIEF DESCRIPTION OF THE DRAWING

The above objects and other advantages of the invention will become apparent upon reading the following description of preferred embodiments and reference to the drawing wherein.

DESCRIPTION OF PREFERRED EMBODIMENTS

Figure 1:
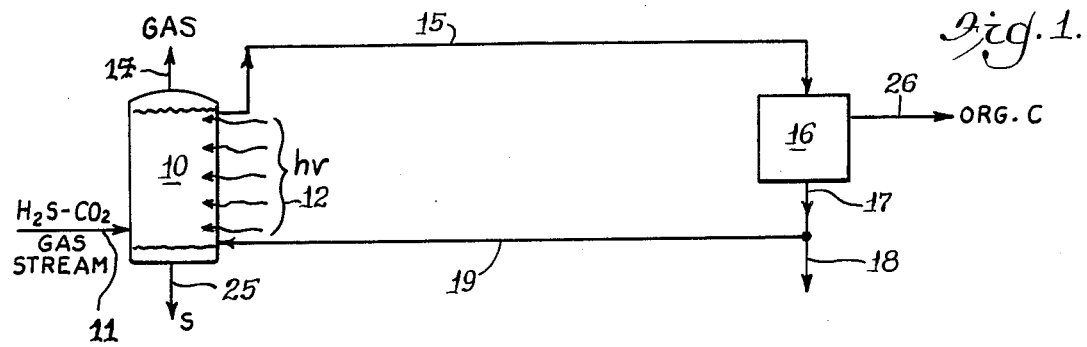
FIG. 1 is a simplified schematic flow diagram of one embodiment of this invention wherein the formed elemental sulfur is withdrawn directly from the photosynthetic bioconversion reactor.

An important aspect of this invention is the photosynthetic bioconversion of reductive sulfur compounds and carbon oxides with an active culture of photosynthetic sulfur bacteria under substantially anaerobic conditions with electromagnetic irradiation forming elemental sulfur and organic carbon compounds. The photosynthetic bioconversion wherein hydrogen sulfide is the reductive sulfur compound and carbon dioxide is the carbon oxide is set forth in the following chemical equation using the photosynthetic sulfur bacteria of the Genus Chlorobium:

$$2H_2S + CO_2 \xrightarrow[\text{Chlorobium}]{\text{electromagnetic radiation}} (CH_2O) + H_2O + 2S$$

It is noted from the above chemical equation that the hydrogen sulfide is the hydrogen donor and sulfur is its oxidized form. Carbon dioxide is the electron acceptor forming the organic carbon compound. It is seen from the stoichiometry of the chemical reaction that 2 moles of hydrogen sulfide are utilized per mole of carbon dioxide. Any photosynthetic sulfur bacteria capable of utilizing a reductive sulfur compound, such as hydrogen sulfide, as its sole source of reducing electrons and carbon oxides, such as carbon dioxide, as its sole source of carbon for organic hydrocarbon production (growth) is suitable. Such photosynthetic sulfur bacteria include those from the Genus Chlorobium. *Chlorobium thiosulfatophilum* is one specific Chlorobium bacteria particularly suited for use in the process of this invention. In the practice of the process of this invention, it is not necessary to use purified and well identified species as long as the majority of the microorganisms provide the above described metabolism. Likewise, the source of the reductive sulfur compound and the carbon dioxide is not important as long as there is at least the stoichiometric amount of carbon dioxide, such as one mole of $CO_2$ for two moles of $H_2S$. It is preferred that the amount of carbon dioxide in the gas stream be in excess of one mole $CO_2$ for 2 moles $H_2S$. When gas streams having high amounts of $H_2S$ are used, $CO_2$ may be added to provide the desired stoichiometric excess. In most process effluent streams, such as acid gas streams, there is a great excess of $CO_2$ which favors the high removal of small amounts of $H_2S$. Although the prior art has taught stoichiometric production of $H_2S$ and $CO_2$ by biological sulfate reduction for Chlorobium action, this is not a necessary feature or contemplated source of $H_2S$ and $CO_2$ for this invention in which high excesses of $CO_2$ are preferred.

The temperature at which the photosynthetic sulfur bacteria exhibit high growth is about 25° to about 45° C., the highest rate of metabolism of the desired materials being at about 28° to about 40° C. The photosynthetic sulfur bacteria exhibit high rates of metabolism in a pH range of about 6 to about 8, preferably about 6.5 to about 7.5. Suitable concentrations of the photosynthetic sulfur bacteria are about 0.5 to about 1.5 grams per liter. Suitable concentrations of $H_2S$ are about 0.1 mole percent to about 65 mole percent, low concentrations of less than about 10 to 15 mole percent $H_2S$ yielding high $H_2S$ conversion rates. Suitable concentrations of $CO_2$ are about stoichiometric amounts to 10 to 1000 times excess stoichiometric $CO_2$. Suitable relationship of $H_2S$ and photosynthetic sulfur bacteria is about 0.045 to about 0.080 mole $H_2S$ per gram bacteria, preferably about 0.055 to about 0.065 mole $H_2S$ per photosynthetic sulfur bacteria. Suitable hydraulic retention times are about 12 to about 36 hours, preferably about 20 to about 30 hours. The pressure at which the bioconversion process of this invention can be carried out is limited only by pressures under which the microorganism cultures can grow and pressure limitations of the equipment. For low pressure processes, the bioconversion process of this invention can be carried out at about ambient pressures and up to about 5 atmospheres, while for higher pressure processes, the bioconversion of this invention can be carried out at pressures as high as the microorganisms metabolize satisfactorily.

The photosynthetic bioconversion may be effected in any suitable anaerobic digestion method known to the art such as a mixed digester, a column in which the bacteria are packed and stabilized so that the gas or liquid is passed through the column for a specified detention time, or the bacteria may be arranged in a fixed bed on solid substrates and the gaseous stream passed through the bed. In the process, the elemental sulfur is excreted by the microorganism during metabolism and settles easily in the clarifier as orthorhombic sulfur and the organic carbon is stored within the microorganism, or upon metabolism in darkness may be excreted by the microorganism as a soluble acetate. Thus, the products of the photosynthetic bioconversion process are elemental sulfur and organically fixed carbon in the form expressed here as $(CH_2O)_n$. The biological action being substantially anaerobic provides the advantage that aeration equipment is not required and there is a low amount of sludge production. The process of this invention may be carried out by a batch system or by using a continuous reaction system.

The wavelengths of electromagnetic energy suitable for irradiation of the photosynthetic sulfur bacteria according to this invention are from about 300 nm to about 1200 nm. Particularly preferred is irradiation near the infrared region, at about 850 nm to about 900 nm. It is preferred that the electromagnetic energy has a continuous spectral distribution in the wavelengths of about 400 nm to about 1000 nm. Suitable sources for providing the above wavelengths and spectral distribution characteristics are sunlight, tungsten incandescent lamps, halogen containing tungsten incandescent lamps, xenon discharge lamps, and fluorescent lamps providing line spectra and continuous spectra. The electromagnetic energy density utilized is determined on the lower end by the rate of photosynthetic activity obtained and on the high end by damage to the microorganism. Generally, about 50 microwatts/cm$^2$ to about 1 watt/cm$^2$.

Referring to FIG. 1, inlet conduit 11 provides sour gas with a mixture of $H_2S$ and $CO_2$ for the process of this invention contained in a gas stream to the lower portion of photosynthetic bioconversion reactor 10. The active liquid volume of photosynthetic bioconversion reactor 10 contains photosynthetic sulfur bacteria, such as Chlorobium thiosulfatophilum, which are irradiated with electromagnetic energy from irradiation source 12. The photosynthetic sulfur bacteria metabolizing under substantially anaerobic conditions with the irradiation by electromagnetic energy converts $H_2S$ to $S^o$, the elemental sulfur being excreted by the microorganism and settling in the lower portion of photosynthetic bioconversion reactor 10 as orthorhombic sulfur. The elemental sulfur may be withdrawn by sulfur conduit 25. The $CO_2$ metabolized by the microorganism forms fixed organic carbon compounds which may be stored by the microorganism as polyglucose or similar organic molecules. Sweet gas substantially free of $H_2S$ is removed by conduit 14. The Chlorobium cells and liquid medium may be withdrawn from the photosynthetic bioconversion reactor 10 through liquid conduit 15 to separator 16. Separator 16 may be any suitable means removing organic carbon compounds from Chlorobium cells, such as by crushing the cells and hollow fiber ultrafiltration or flotation, and providing organic carbon compounds which may be withdrawn through organic carbon removal conduit 26. The Chlorobium cells and liquid are removed from the separator through conduit 17 and microorganism cells and excess liquid may be removed from the system through removal conduit 18 and microorganism cells and liquid recycled through recycle conduit 19 to photosynthetic bioconversion reactor 10.

Figure 2:
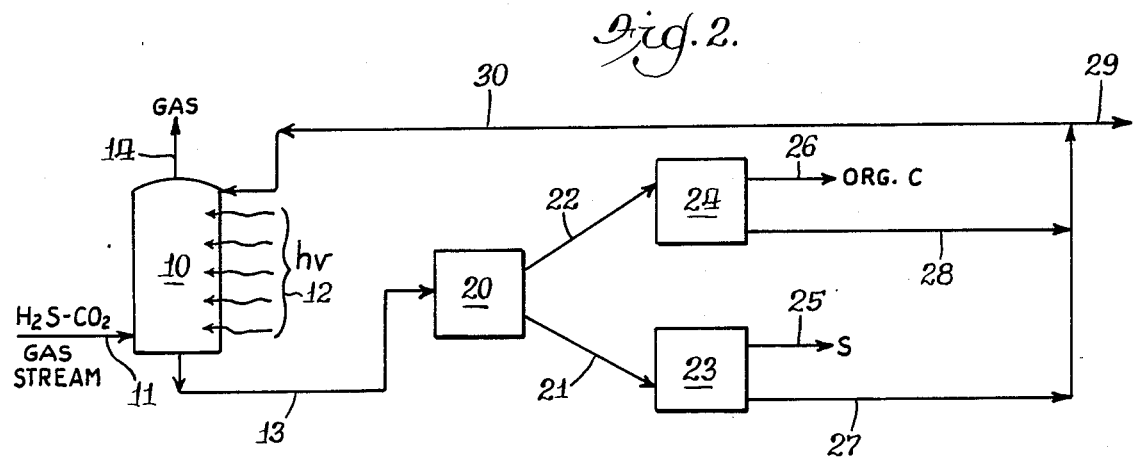
FIG. 2 is a simplified schematic flow diagram of another embodiment of the process of this invention.
Figure 3:
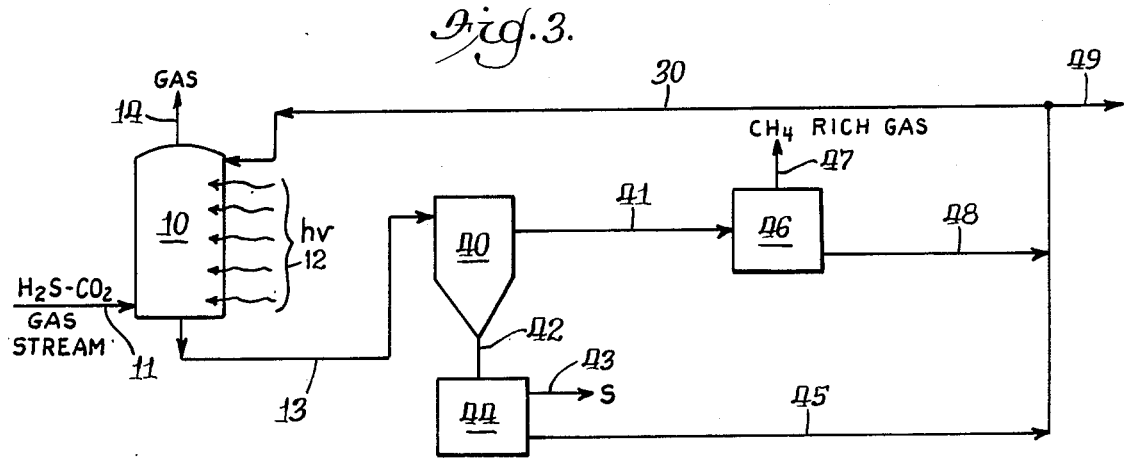
FIG. 3 is a simplified schematic flow diagram of another embodiment of the process of this invention utilizing two phase anaerobic digestion.
Figure 4:
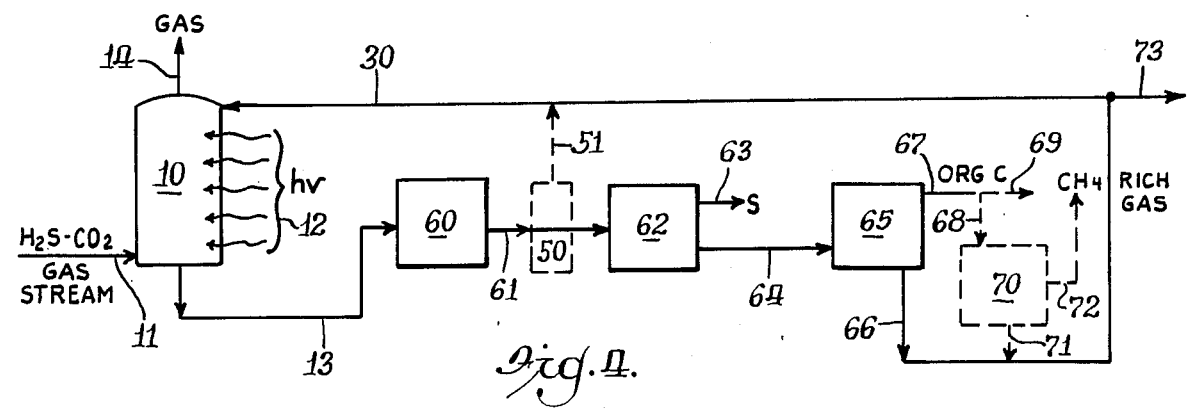
FIG. 4 is another simplified schematic flow diagram of another embodiment of this invention utilizing a dark reactor to simplify separation of the products of photosynthetic bioconversion.

FIGS. 2-4 show preferred embodiments for combination of various manners of treating the product of the photosynthetic bioconversion reactor, particularly when using a continuous flow reactor such as a fluidized bed photosynthetic bioconversion reactor 10.

FIG. 2 shows inlet conduit 11 for supply of the sour gas stream containing hydrogen sulfide and carbon dioxide to photosynthetic bioconversion reactor 10. The stream containing hydrogen sulfide and carbon dioxide is treated by the photosynthetic bioconversion bacteria within reactor 10 and sweet gas conduit 14 provides exit of the gas stream, substantially free of reductive sulfur compounds, from photosynthetic bioconversion reactor 10 following suitable bioconversion treatment as described above. Most of the acid-gas streams for treatment by this process will have a stoichiometric excess of carbon dioxide which cannot be metabolized by the photosynthetic sulfur bacteria and will pass from reactor 10 with the clean gas stream through gas conduit 14. In the embodiment shown in FIG. 2, product conduit 13 withdraws liquid comprising liquid culture media, active bacteria, metabolized elemental sulfur, and organic carbon compounds to separator 20. Separator 20 is any suitable separator means for separation of the elemental sulfur portion of the liquid stream with a small amount of the remaining components, which sulfur containing portion is passed through conduit 21 to separator 23 for final separation of the solid elemental sulfur from the remaining other components. The elemental sulfur portion is withdrawn through sulfur conduit 25 and the remaining component is withdrawn from separator 23 through liquid conduit 27. The predominantly liquid product from separator 20 is passed through conduit 22 to separator 24 for final separation of the organic carbon compounds from the liquid portion of the product stream. The separated organic carbon compounds are withdrawn through organic carbon removal conduit 26 and the remaining liquid component is withdrawn through liquid conduit 28. Liquid off conduit 29 is provided for withdrawal of liquid and cells from the system, necessary due to the increasing water content of the system formed by the photosynthetic reaction, and recycle conduit 30 for recycle of liquid and microorganism cells to photosynthetic bioconversion reactor 10. Suitable apparatus for separators 20, 23 and 24 include centrifugal separators and rotary filters.

FIG. 3 shows one embodiment of this invention therein the organic carbon compounds produced by the photosynthetic sulfur bacteria are largely converted to methane containing gas by anaerobic methanogenic digestion. It is advantageous to use two-phase anaerobic digestion employing acid phase digester 40 and methane phase digester 46. Any suitable anaerobic digestion process producing the desired methane content gas may be used, however, the two-phase anaerobic digestion as is known to the art, for example, as taught by U.S. Pat. No. 4,022,665, is particularly advantageous in providing for removal of the elemental sulfur. As shown in FIG. 3, product from photosynthetic bioconversion reactor 10 is transported through product conduit 13 to acid phase digester 40 for fermentation under anaerobic conditions which efficiently breaks down the organic carbon materials to primarily acetates which are water soluble for more efficient methanation and easy separation for transfer through organic carbon conduit 41 to methanogenic reactor 46. The solid elemental sulfur is removed from acid phase digester 40 through conduit 42 to separator 44 for final separation and removal of the elemental sulfur by sulfur conduit 43 and removal of remaining liquid through liquid conduit 45. Methanogenic fermentation is carried out in methane phase digester 46 with produced methane containing gas being removed through methane removal conduit 47 and liquid residue being removed through liquid conduit 48. To adjust the liquid flow, liquid off conduit 49 is provided to remove liquid from the system and recycle conduit 30 is provided for liquid recycle to photosynthetic bioconversion reactor 10. This embodiment provides a substantially sulfur free gas, separated elemental sulfur and utilization of $CO_2$ in the gas stream to form useful organic carbon compounds readily converted to methane containing gas. The process being low temperature and producing a useful fuel is an energy efficient process.

Another advantageous embodiment of the process of this invention is shown in FIG. 4. In the embodiment shown in FIG. 4, the products from photosynthetic bioconversion reactor 10 are passed through product conduit 13 to dark phase bioconversion reactor 60 wherein stored Chlorobium glucose is converted to soluble extracellular acetate. Chlorobium are known to store significant amounts of carbon synthesized as cellular polyglucose which, in the absence of light, is metabolized and excreted as principally hydrocarbon acids, with 80 percent being acetic acid. Detention time in the dark phase is about the same period of time as in the light phase or about 12 to about 36 hours hydraulic detention, preferably about 20 to about 30 hours. The acetic acid excreted from the cells is soluble in water for easy separation from both the Chlorobium cells and the elemental sulfur. The products of the dark reaction are passed through product conduit 61 to separator 62 for final separation of elemental sulfur by sulfur conduit 63. An alternative is to have cell separator 50 in line 61 for separation of Chlorobium cells for recycle through conduit 51 to recycle conduit 30. The liquid portion may then be passed through liquid conduit 64 to separator 65 where the Chlorobium cells are separated from the fixed organic carbon and withdrawn through conduit 66 for recycle through conduit 30 to photosynthetic bioconversion reactor 10 or withdrawn from the process through product conduit 73 as a biomass product. The fixed organic carbon portion may be passed through organic carbon conduit 67 and either withdrawn from the process through organic carbon off-conduit 69 or passed through alternative organic carbon conduit 68 to alternative anaerobic methanogenic digester 70 for formation of methane gas for withdrawal by gas off-conduit 72, the liquid residue being passed by liquid conduit 71 to the recycle circuit. Suitable apparatus for separators 62 and 65 include centrifugal separators and rotary filters.

From the above description it is seen that the process of this invention provides a low temperature, low pressure, energy efficient process for removal of sulfur from a wide variety of gaseous and liquid streams providing two useful products, elemental sulfur and organic carbon compounds useful as such or in combination with conversion to gaseous hydrocarbon fuels. The process of this invention, particularly in combination with two-phase anaerobic digestion or dark phase Chlorobium metabolism provides products which are easily separable and excreted from the cells so that the microorganisms do not have to be broken open. Essentially complete hydrogen sulfide removal is possible thereby eliminating the need for expensive tail gas desulfurization as is necessary with many current sulfur removing processes. The process of this invention is unlike other industrial fermentations such as used in the production of drugs, alcohol and other chemicals, does not require sterilization procedures because the photosynthetic sulfur bacteria are the only microorganisms reported which survive in an anaerobic environment purged with greater than 60 gram moles of $H_2S$ per liter per 24 hours and thus the $H_2S$ is acting as a specific bactericide, inhibiting the growth of any potential contaminating anaerobic microorganisms, such as methane producing bacteria. Thus, only one type of microorganism is growing in the photosynthetic bioconversion reactor simplifying process control and quality control. One important aspect of this invention is the production of sulfur and useful organic carbon compounds from acid-gas environments such as from coal or oil hydrogasification or hydroliquefaction processes and natural gas streams. The product of the amine (or other alkaline absorbing solution) stripper used in acid-gas removal processes is suitable for direct feed to the photosynthetic bioconversion reactor of this invention. It is also practical for the photosynthetic sulfur bacteria to adapt to the raw gas from a hydrogasifier, such as would contain $H_2$, $CH_4$, $CO$, $CO_2$, $H_2S$, $HCN$, $N_2$, $NH_3$, $CS_2$, $COS$, and various volatile organic and organosulfur compounds. This would provide further advantages to the process of this invention permitting elimination of the gas scrubbers, such as the alkaline solution gas scrubbers. Further, the process of the present invention does not require chemical solutions which can be corrosive, such as amines, or expensive catalysts.

The following Example is set forth to specifically illustrate one embodiment of this invention and should not be considered to limit the invention.

EXAMPLE

A 1 liter pyrex glass (Virtis BSF 500) laboratory scale batch reactor was set up with 800 cc liquid volume and 200 cc headspace. An active anaerobic culture, principally Chlorobium thiosulfatophilum was established in the liquid volume at 30° C. and pH 6.5-7.0 by an initial inoculum of 22.5 $\mu M/L$ Chlorobium chlorophyll. Although the total volume of the reactor is 800 ml, the chemical constituents of the medium were defined in g/L:$KH_2PO_4$, 0.4; $NH_4Cl$, 0.4; $MgCl_26H_2O$, 2.0; $NaCl$, 1.6; $CaCl_2$, 0.016; $FeSO_4.7H_2O$, 2 ml of 5% $FeSO_4.7H_2O$ in 0.4N HCl. Trace elements stock solution A (1.0 ml/L) and stock solution B (0.8 ml/L) were subsequently added to the minimal salts medium. Stock solution A is a modification of Larsen's trace elements (1952), and consists of (g/L); $FeCl_3$, 1.6; $Na_2B_4O_7.10H_2O$, 0.80; $ZnSO_4.7H_2O$, 0.44; $CoSO_4.7H_2O$, 0.24; $CuCl_2.2H_2O$, 0.135; $MnSO_4H_2O$, 0.0165; Fe-EDTA solution, 110 ml. (Fe-EDTA solution is prepared by adding 24.9 g $FeSO_4.7H_2O$ and 59 gm of EDTA to a total volume of 1000 ml and adjusting the pH to 9.7 with 0.1 N NaOH.) Trace elements stock solution B as described by Olson et al (1973) consists of (g/L): $H_3BO_4$, 2.90; $MnCl_2.4H_2O$, 1.80; $ZnSO_4.7H_2O$, 0.22; $CuSO_4.5H_2O$, 0.079; $NaMoO_40.2H_2O$, 0.25; $NH_4VO_3$, 0.023; $Co(NO_3)_20.6H_2O$, 0.049. Finally, 33 ml from a 0.4 M $NaH_2PO_4$ stock solution and 67 ml from a 0.4 M $Na_2HPO_4$ stock solution were added and the broth volume brought to 400 ml with deionized water. A 50% inoculum of 400 ml of freshly grown Chlorobium cells containing 450 $\mu M/L$ Chlorobium chlorophyll was added to the chemically defined medium. A mixed gas stream of 4.2 mole percent $H_2S$, 8.4 mole percent $CO_2$, and 87.4 mole percent $N_2$ was sparged into the liquid volume through a glass frit at a rate of 24 cc/minute, providing 79mM/liter/24 hours $H_2S$ going into the system with constant stirring of the liquid with a magnetic stir bar. The active volume of the reactor was irradiated with light from a 150 watt flood lamp at about 5 cm from the center of the reactor. The active bacterial culture was maintained under growth conditions for a detention time of 24 hours with pressure at less than 1.1 atmosphere pressure within the reactor. Gas was continually withdrawn from the headspace and passed in sequence through a zinc acetate trap for sulfide absorption with $H_2S$ determination by a methylene blue analysis, concentrated $H_2SO_4$ trap for water removal and ascarite trap for $CO_2$ determination and released. Analysis of the zinc acetate trap liquid contents showed 0.1mM/liter/24 hours $H_2S$ leaving the reactor, or approximately 100 percent $H_2S$ removal as elemental sulfur with approximately stoichiometric amounts of organic hydrocarbon formation and Chlorobium chlorophyll increase to 550 $\mu M/L$.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A photosynthetic bioconversion process for removal of sulfur compounds from a gas stream comprising carbon oxide and reductive sulfur compounds, comprising the steps:

contacting said gas stream comprising carbon oxide compounds and reductive sulfur compounds with an active culture of photosynthetic bacteria capable of utilizing said reductive sulfur compound as its sole source of reducing electrons and said carbon oxides as its sole source of carbon for growth under substantially anaerobic conditions with electromagnetic radiation wherein said reductive sulfur compound provides the sole source of reducing electrons and said carbon oxides provide the sole source of carbon for growth and cultivating said bacteria to form elemental sulfur and organic carbon compounds;

passing said formed elemental sulfur and organic carbon compounds together with said photosynthetic sulfur bacteria to a dark phase reactor for further metabolism of said organic carbon compounds to form and excrete from said bacteria predominately lower organic acids; and separately removing said elemental sulfur and said lower oganic acids.

2. The process of claim 1 wherein the hydraulic detention time in the dark phase is about 12 to 36 hours.

3. The process of claim 1 wherein the hydraulic detention time in the dark phase is about 20 to about 30 hours.

4. The process of claim 1 wherein said photosynthetic sulfur bacteria are *Chlorobium*.

5. The process of claim 1 wherein said reducing sulfur compounds are predominantly hydrogen sulfide and said carbon oxides are predominantly carbon dioxide, said carbon dioxide being present in stoichiometric excess.

6. The process of claim 1 wherein said bacteria are *Chlorobium thiosulfatophilum*.

7. The process of claim 1 wherein said cultivating is at temperatures of about 25° to about 45° C.

8. The process of claim 1 wherein said cultivating is at a pH of about 6 to about 8.

9. The process of claim 1 wherein said *Chlorobium* are present in concentrations of about 0.5 to about 1.5 grams per liter.

10. The process of claim 1 wherein the hydraulic detention time is about 12 to about 36 hours.

11. The process of claim 1 wherein said irradiation is with electromagnetic energy at wavelengths of about 300 to about 1200 nm.

12. The process of claim 1 wherein said process is carried out at pressures of about ambient to about 5 atmospheres.

13. The process of claim 1 wherein said hydrogen sulfide comprises less than 10 mole percent of said gas stream and greater than 95 percent of the sulfur of said hydrogen sulfide is converted to elemental sulfur.

14. The process of claim 1 wherein said hydrogen sulfide is introduced in a concentration of about 0.045 to about 0.080 Mole $H_2S$ per gram bacteria.

15. The process of claim 4 wherein said cultivating is at temperatures of about 25° to about 45° C., pH about 6 to about 8, said *Chlorobium* are present in concentrations of about 0.5 to about 1.5 grams per liter, hydraulic detention time is about 12 to about 36 hours, said irradiation is with electromagnetic energy at wavelengths of about 400 to about 1000 nm, said hydrogen sulfide is introduced in a concentration of about 0.045 to about 0.080 Mole $H_2S$ per gram bacteria; and the hydraulic detention time is about 12 to about 36 hours converting greater than about 95 percent of the hydrogen sulfide to elemental sulfur.

* * * * *